(12) United States Patent
Caillouette

(10) Patent No.: US 6,406,441 B1
(45) Date of Patent: Jun. 18, 2002

(54) VAGINAL TEST APPARATUS AND METHOD

(76) Inventor: James C. Caillouette, 685 Oak Knoll Cir., Pasadena, CA (US) 91106

( * ) Notice: Subject to any disclaimer, the term of this patent is extended or adjusted under 35 U.S.C. 154(b) by 0 days.

(21) Appl. No.: 09/499,296

(22) Filed: Feb. 7, 2000

Related U.S. Application Data

(63) Continuation-in-part of application No. 09/118,502, filed on Jul. 17, 1998, now Pat. No. 6,117,090, and a continuation-in-part of application No. 09/072,257, filed on May 4, 1998, now Pat. No. 6,013,036, which is a continuation-in-part of application No. 08/789,484, filed on Jan. 27, 1997, now Pat. No. 5,827,200, and a continuation-in-part of application No. 08/789,835, filed on Jan. 31, 1997, now Pat. No. 5,782,801, which is a continuation-in-part of application No. 08/890,748, filed on Jul. 11, 1997, now Pat. No. 5,916,176, which is a continuation-in-part of application No. 08/699,251, filed on Aug. 19, 1996, now Pat. No. 5,735,801, which is a continuation-in-part of application No. 08/570,534, filed on Dec. 11, 1995, now Pat. No. 5,762,614, which is a continuation-in-part of application No. 08/537,379, filed on Oct. 27, 1995, now Pat. No. 5,577,512, which is a continuation-in-part of application No. 08/376,830, filed on Jan. 23, 1995, now Pat. No. 5,664,579, which is a continuation-in-part of application No. 08/295,399, filed on Aug. 25, 1994, now Pat. No. 5,425,377.

(51) Int. Cl.[7] .................................................. A61B 5/00
(52) U.S. Cl. ....................................................... 600/584
(58) Field of Search ................................. 600/562, 570, 600/572, 573, 584

(56) References Cited

U.S. PATENT DOCUMENTS

| | | |
|---|---|---|
| 2,664,879 A | 1/1954 | Hardy |
| 2,945,491 A | 7/1960 | Gibbs |
| 3,013,656 A | 2/1961 | Murphy, Jr. |
| 3,037,496 A | 6/1962 | Melges |
| 3,117,569 A | 1/1964 | Wegner |
| 3,319,621 A | 5/1967 | Schwerin |

(List continued on next page.)

FOREIGN PATENT DOCUMENTS

WO    WO-A-97/46878    12/1997

OTHER PUBLICATIONS

"Vulvovaginitis", Ronald M. Meltzer, vol. 1, Chapter 37, 1994.
"Urinary Incontinence And Related Urogenital Symptoms In Elderly Women", Ulla Molander, Scandinavian Association of Obstetricians and Gynecologists, Supplement 158, vol. 72, 1993.
"Estrogen Deprivation And Vaginal Function In Postmenopausal Women", James P. Semmens, MD, Gorm Wagner, MD, 1982.
"The Estradiol Vaginal Ring—A Study of Existing Clinical Data" Gloria Bachmann, Maturitas 22 Suppl. (1995) S21–S29, 1995.
"Estrogens and the Urogenital Tract", Peter Smith, Dept. of Obstetrics & Gynecology, University Hospital, S–751 85 Uppsala, Sweden, 1993.
"Nonspecific Vaginitis—Diagnostic Criterial and Microbial and Epidemiologic Associations", Richard Amsel, MD et al, The American Journal of Medicine, vol. 74, Jan., 1983.
"Biochemical Diagnosis of Vaginitis: Determination of Diamines in Vaginal Fluid", Kirk C.S. Chen et al, The Journal of Infectious Diseases, vol. 145, No. 3, Mar., 1982.
"Amine Content of Vaginal Fluid from Untreated and Treated Patients with Nonspecific Vaginitis", Kirk C.S. Chen et al, The American Society For Clinical Investigation, Inc., vol. 63, May, 1979, pp. 828–835.

*Primary Examiner*—Max Hindenburg
(74) *Attorney, Agent, or Firm*—William W. Haefliger

(57) ABSTRACT

Vaginal probe apparatus comprising in combination a longitudinally elongated probe insertible into the vagina for a test purpose; a support operatively connected with the probe projecting away from the support, the support including a manually manipulable handle; and an edge presented generally longitudinally for limiting probe insertion into the vagina.

26 Claims, 3 Drawing Sheets

U.S. PATENT DOCUMENTS

| | | |
|---|---|---|
| 3,450,129 A | 6/1969 | Avery et al. |
| 3,507,269 A | 4/1970 | Berry |
| 3,509,872 A | 5/1970 | Truhan |
| 3,777,743 A | 12/1973 | Binard et al. |
| 3,792,699 A | 2/1974 | Tobin et al. |
| 4,010,738 A | 3/1977 | Preti et al. |
| 4,384,587 A * | 5/1983 | Milgrom .................... 600/570 |
| 4,409,182 A | 10/1983 | Macklem |
| 4,457,313 A | 7/1984 | Alter |
| 4,784,158 A | 11/1988 | Okimoto |
| 4,788,985 A | 12/1988 | Manning et al. |
| 4,820,259 A | 4/1989 | Stevens |
| 4,862,899 A | 9/1989 | Bucaro |
| 5,063,930 A | 11/1991 | Nucci |
| 5,147,288 A | 9/1992 | Schiavo |
| 5,425,377 A | 6/1995 | Caillouette |
| 5,660,790 A | 8/1997 | Lawrence et al. |
| 5,664,579 A | 9/1997 | Caillouette |
| 5,738,634 A | 4/1998 | Caillouette |
| 5,762,614 A | 6/1998 | Caillouette |
| 5,782,801 A | 7/1998 | Caillouette |
| 5,827,200 A | 10/1998 | Caillouette |

* cited by examiner

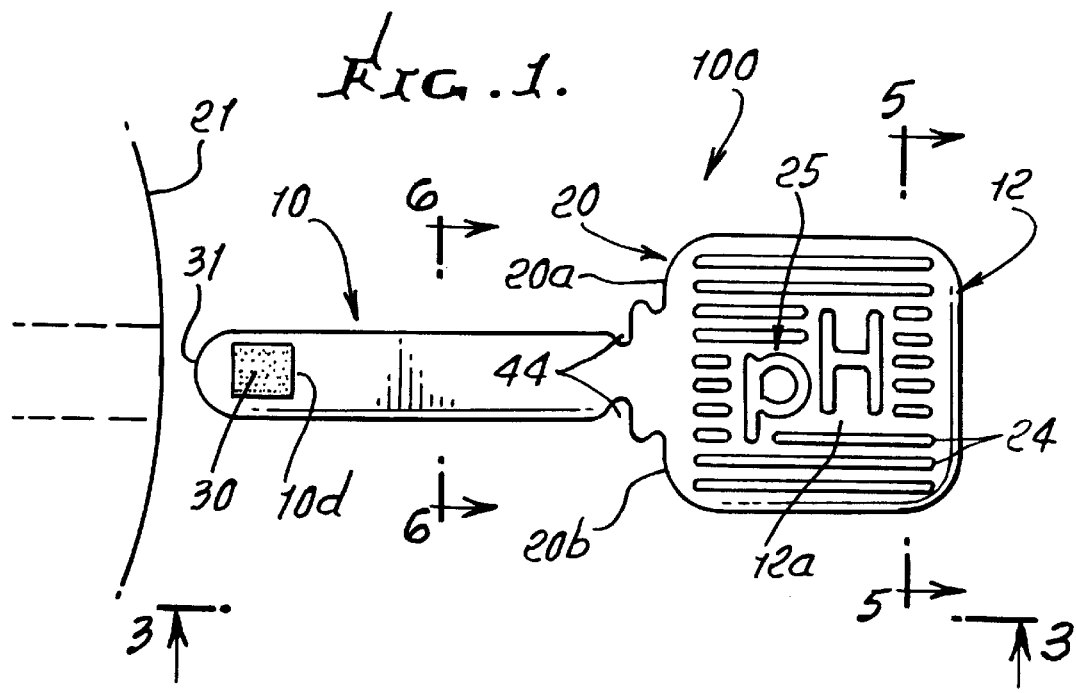
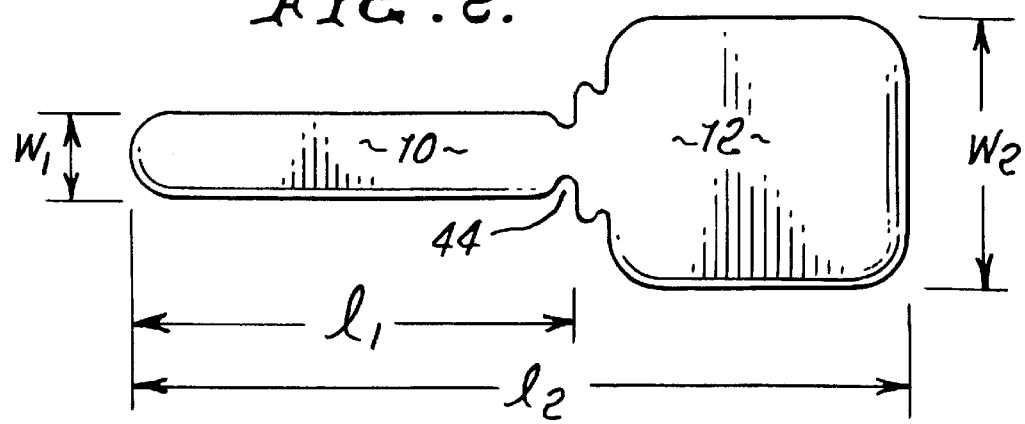
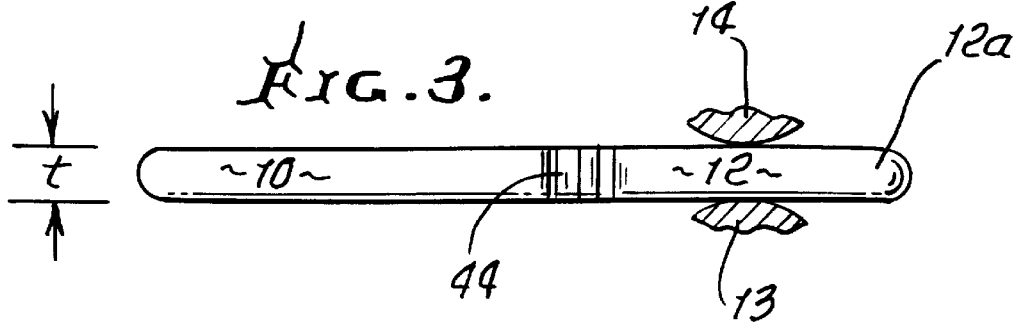

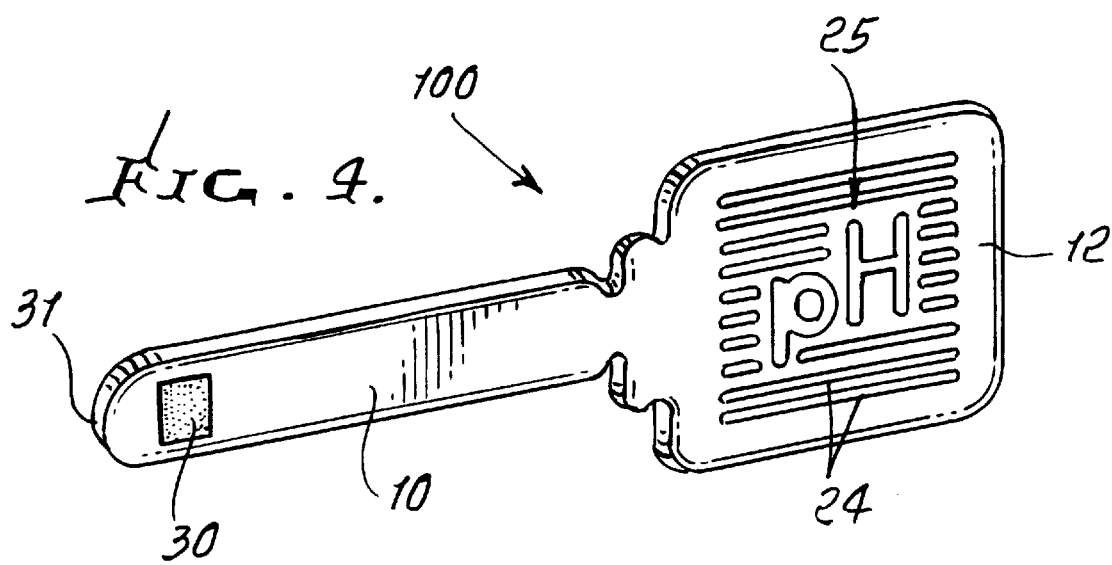
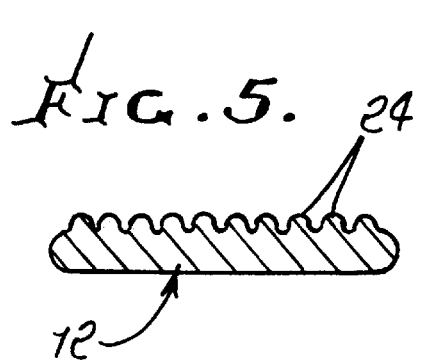
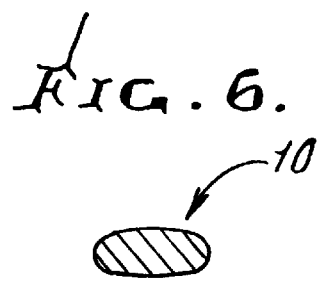
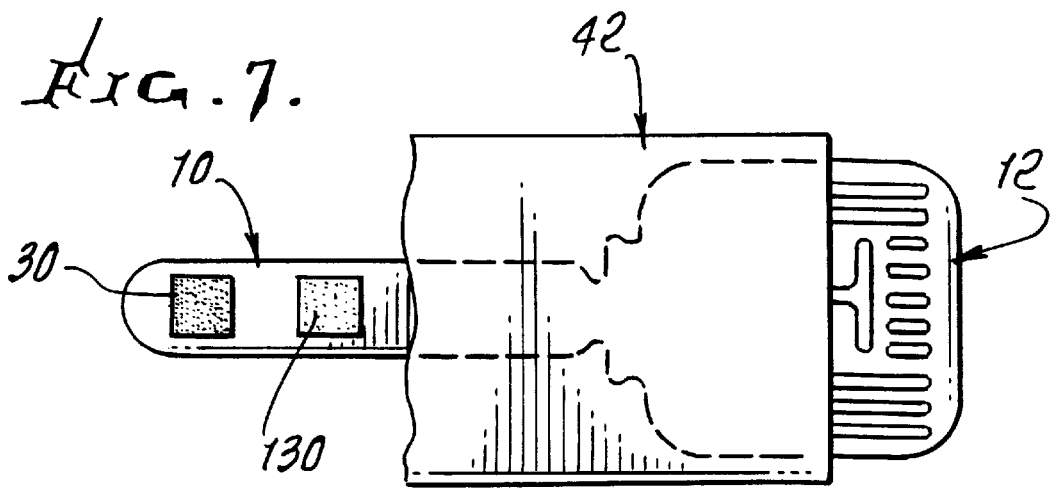

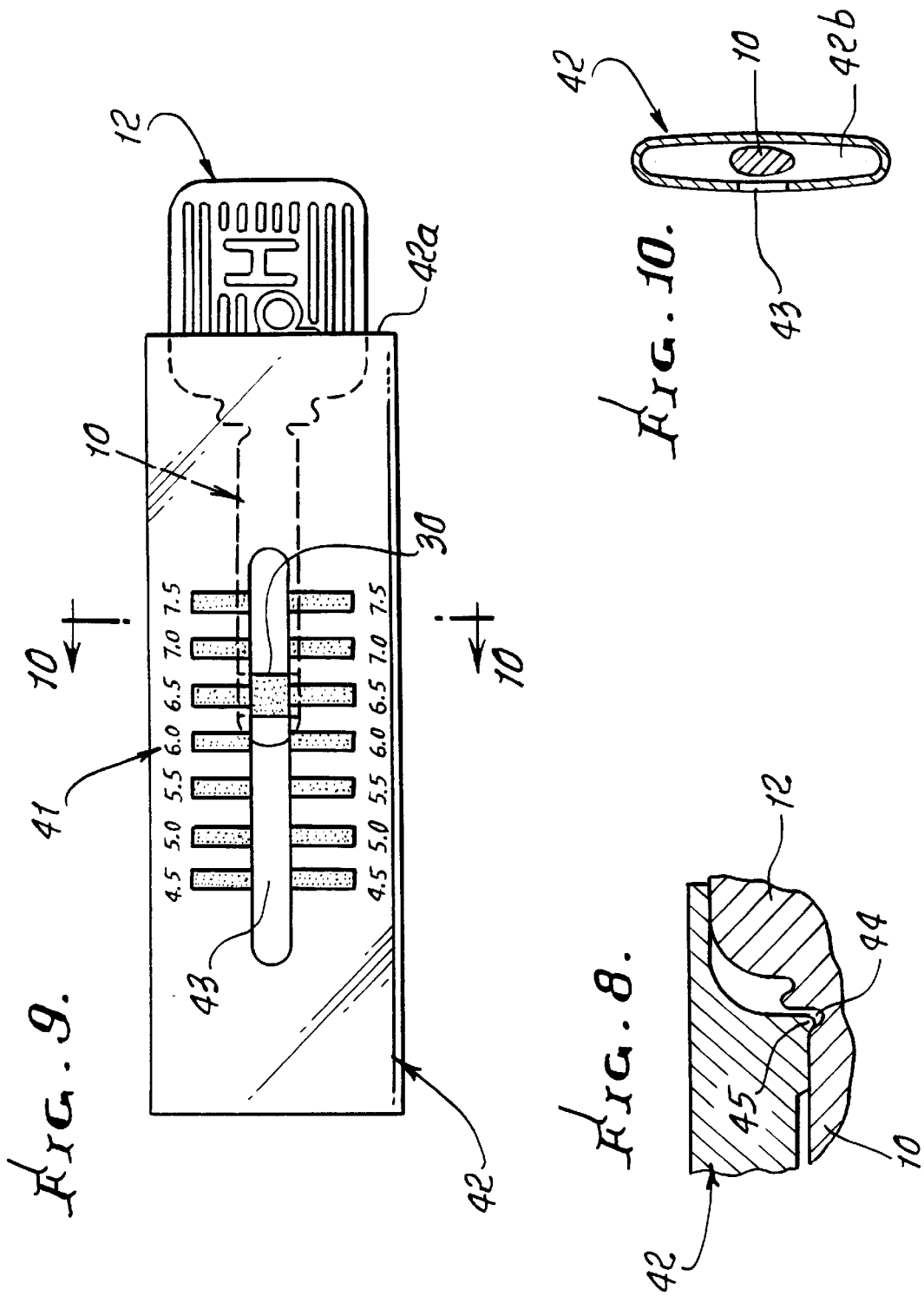

VAGINAL TEST APPARATUS AND METHOD

This application is a continuation-in-part of prior U.S. application Ser. No. 09/118,502 filed Jul. 17, 1998 now U.S. Pat. No. 6,117,090 which is a continuation-in-part of prior U.S. application Ser. No. 08/789,484 filed Jan. 27, 1997, now U.S. Pat. No. 5,827,200, and a continuation-in-part of prior U.S. application Ser. No. 08/789,835 filed Jan. 31, 1997, now U.S. Pat. No. 5,782,801, and this application is also a continuation-in-part of prior U.S. application Ser. No. 09/072,257 filed May 4, 1998, now U.S. Pat. No. 6,013,036, which is a continuation-in-part of prior U.S. application Ser. No. 08/890,748 filed Jul. 11, 1997, now U.S. Pat. No. 5,916,176, which is a continuation-in-part of prior U.S. application Ser. No. 08/699,251 filed Aug. 19, 1996, now U.S. Pat. No. 5,735,801, which is a continuation-in-part of prior U.S. application Ser. No. 08/570,534 filed Dec. 11, 1995, now U.S. Pat. No. 5,762,614, which is a continuation-in-part of prior U.S. application Ser. No. 08/537,379 filed Oct. 27, 1995, now U.S. Pat. No. 5,577,512, which is a continuation-in-part of prior U.S. application Ser. No. 08/376,830 filed Jan. 23, 1995, now U.S. Pat. No. 5,664,579, which is a continuation-in-part of prior U.S. application Ser. No. 08/295,399 filed Aug. 25, 1994, now U.S. Pat. No. 5,425,377.

BACKGROUND OF THE INVENTION

This invention relates generally to testing of body fluid, one example being pH measurement of body fluid, such as vaginal and/or urethral fluid, or moisture, and more particularly, to a rapid, easily performed method of such testing, or obtaining such measurement.

There is continued need to obtain pH measurement of vaginal fluid, as for example in the determination of whether amniotic fluid has escaped into the vagina, during late pregnancy. Amniotic fluid is normally alkaline, whereas vaginal moisture is normally acidic. This difference enables testing for pH, using a test strip, such as a Nitrazine® strip, typically handled by forceps when inserted into the vagina, urethra or other body openings for pH test purposes; however, the procedure and subsequent procedures to determine acidity or alkalinity requires considerable manipulation, including cutting of a test strip, grasping of the cut strip by forceps manipulation, subsequent insertion with risk of separation of the strip from the forceps, recovery of the strip, and its examination. There is also need to obtain pH measurement of urethral moisture; to test for need for estrogen treatment, and to test for presence of pathogenic bacteria.

Further, there is need for a simple, rapidly carried out method which obviates problems associated with the conventional procedure one example being need to assuredly test vaginal moisture within the vagina, but spaced from the cervix.

SUMMARY OF THE INVENTION

It is a major object of the invention to provide a significantly improved vaginal probe apparatus which meets the above need, and overcomes prior problems, as referred to. Basically, the apparatus of the invention includes:
   a) a longitudinally elongated probe insertible into the vagina, for a test purpose,
   b) a support operatively connected with the probe projecting away from the support,
   c) the support including:
      i) a manually manipulable handle,
      ii) an edge presented generally longitudinally for limiting probe insertion into the vagina.

Another object is to provide the probe and support to have a key-like configuration, enhancing effective use. The support may have surface irregularities on the support for engagement by the thumb or finger of a user; and some irregularities may comprise protuberances, at one side of the support.

Recognizing that the sizes of the probe and support are important, the probe may typically have length "l" between 1½ and 2½ inches; and a width "w" between ¼ and ½ inch.

A further object includes provision of at least one vaginal moisture wettable test element on the probe; and that element may advantageously comprise one or more indicator or test elements, such as:
   i) a pH indicator
   ii) an amine indicator
   iii) a bacteria indicator.

In this regard, the one or more of the indicators or test elements may comprise a moisture absorber, for use in a test after removal from the vagina or urethra.

Yet another object includes provision of at least one locking projection on the probe, to interlock with a storage sheath into which the probe is receivable.

For ease of use, the probe may define a longitudinally extending axis which substantially bisects the support; alternatively, the support may extend eccentrically relative to the axis of the probe.

An added object is to provide a method of using vaginal probe apparatus comprising, in combination
   a) a longitudinally elongated probe insertible into the vagina, for a test purpose,
   b) a support operatively connected with the probe projecting away from the support,
   c) the support including:
      iii) a manually manipulable handle,
      iv) an edge presented generally longitudinally for limiting probe insertion into the vagina,
   d) the method including inserting the probe into the vagina until said edge engages the body, to achieve said test purpose associated with an indicator at the side of the probe,
   e) and withdrawing the probe from the vagina for use of the indicator to complete the test purpose.

In this regard, the probe and support may have key-like configuration with use advantages. The method further contemplates grasping the support rearward of the edge, during insertion limiting steps d) and e).

These and other objects and advantages of the invention, as well as the details of an illustrative embodiment, will be more fully understood from the following specification and drawings, in which:

DRAWING DESCRIPTION

FIG. 1 is a top plan view of a probe and support incorporating the invention;

FIG. 2 is a bottom plan view of the FIG. 1 probe and support;

FIG. 3 is an edge view taken on lines 3—3 of FIG. 1;

FIG. 4 is a perspective view of the FIG. 1 probe and support;

FIG. 5 is a section taken on lines 5—5 of FIG. 1;

FIG. 6 is a section on line 6—6 of FIG. 1;

FIG. 7 is a view of the FIG. 1 probe received in a protective sheath;

FIG. 8 is a fragmentary view showing interlocking of the sheath and probe;

FIG. 9 is an enlarged view showing details of the sheath, with probe viewing window, and color comparison measurement zones, on the sheath; and also showing comparison of a color change of a test element with different colored zones on a sheath or other carrier; and FIG. 10 is a section taken on lines 10—10 of FIG. 9.

DETAILED DESCRIPTION

Referring first to FIG. 1, it shows a preferred device:
a) a longitudinally elongated probe insertible into the vagina, for a test purpose,
b) a support operatively connected with the probe projecting away from the support,
c) the support including:
 i) a manually manipulable handle,
 ii) and an edge presented generally longitudinally for limiting probe insertion into the vagina.

As shown, the probe 10 of the apparatus 100 protrudes lengthwise from the support 12, which defines a handle 12a that can be easily gripped between the thumb 13 and forefinger 14 of the user, as seen in FIG. 3. The probe and support preferably have key-like configuration, as shown.

Forwardly or longitudinally presented edge 20 of the support limits insertion of the probe, as by engagement with the body 21, and dual edges may be provided as at 20a and 20b, at opposite lateral sides of the probe, for that purpose. The apparatus 100 may for example consist of plastic, metal or compressed fiber (example paper).

Surface irregularities may be provided on one laterally facing side of the support, and such irregularities are shown to extend longitudinally to be grasped by the thumb and prevent lateral slippage, relative to the user's thumb. The irregularities are shown in the form of protuberances 24 which are laterally spaced apart. A "pH" monogram or escutcheon may be provided as seen at 25, to be indicative of ease and comparability for testing or measuring vaginal moisture pH. The monogram may also be sited to indicate the side of the support on which a test element 30 (as described below) is located.

The probe and support, or handle have the following dimensions for best results:

probe overall length "$l_1$"=1½ to 2½ inches
probe width "$w_1$"=¼ to ½ inch
support width $w_2$=¾ to 1½ inch
thickness "t"=3/16 to 5/16 inch
overall length $l_2$ of probe and support =3¼ to 3¾ inches.
Preferably, $l_1 \cong 2$ inches
 $w_1 \cong$ ⅜ inch
 $w_2 \cong 1$¼ inch
 $l_2 \cong 3$½ inch.

Also, the probe has an approximately flat, oval cross section, as seen in FIG. 6.

FIG. 1 also shows a test element 30 at the side of the probe, near its tip 31, to be pressed toward and against the vaginal wall. Element 30 (located for example on the same lateral side as the test element 30) typically comprises an indicator element, as for example one of the following:
 i) a pH indicator
 ii) an amine indicator
 iii) a bacteria indicator.

The pH indicator or detector typically takes the form of a Nitrazine® strip adhered to the side of the probe, as for example by double sided adhesive tape. After exposure of the strip to vaginal moisture, its changed color (according to pH level) is compared with the series 41 of bands on a sheath 42, as seen in FIG. 9. Each band has a different color corresponding to a pH level color to which the detector strip may change. See for example the indicated pH levels 4.5, 5.0, 5.5, 6.0, 6.5, 7.0 and 7.5 adjacent the color bands. The bands may be provided on a strip adhered to the outer surface of the sleeve or receptacle 42. Paper strips providing such elements are known, and sold under the name HYDRION papers, by Micro Essential Laboratory Inc., Brooklyn, N.Y. 11210. The band for pH 4.5 is typically bright yellow; the band for pH 6.0 is olive in color; and the band for pH 7.5 is navy blue. The color of at least a side portion 10d of the probe itself, near the indicator strip 30, may be colored to correspond to the color of the indicator strip at pH 4.5, to indicate a NORMAL condition. For example, when a Nitrazine® strip 30 is used, as on a plastic probe, the probe surface at 10d, (or the entire probe, or the entire device 100) can be sunflower yellow, in color, to correspond to the color of the Nitrazine® strip at pH 4.5.

In use, the probe 10 and sleeve or receptacle 42 are relatively moved, lengthwise, to bring the detector strip 30 (after its exposure to moisture and color change as referred to above) into lateral registration with the color comparison bands, enabling ready visual comparison of the color of the detector strip with the closest color of one of the bands, enabling a pH determination. For this purpose, a window zone 43 of the carrier sleeve adjacent the bands may be transparent to allow visual observation of the detector, through that zone, adjacent the bands. The entire sleeve and the strip 30 may be transparent.

Prior to use, the right end 42a of the receptacle is opened, and the carrier probe 10 is withdrawn from space 42b, for use in gathering vaginal moisture on 10. Thereafter, the probe is re-inserted into the elongated receptacle 42, to bring indicator 30 under the window 43. The probe and indicator 30 preferably have width greater than the window width, so that indicator 30 adjacently registers with the successive bands in the two rows as the probe moves longitudinally. This facilitates ease of color comparison of the indicator with the bands. After such color comparison use, the indicator and probe may remain in the receptacle, for ease of disposal, or storage.

The test element 30 may alternatively comprise a porous body which may be mounted or carried as at near one end of the probe, to receive vaginal moisture. The color changing reactant may be applied to or incorporated on, or in the interstices of the receiver, and may consist, for example, of one or more of the following: Bromocresol Green, Bromocresol Purple, Nitrazine Yellow, Bromophenol Blue, and equivalents.

The reactant may ultimately be brought into contact with the receiver after its removal from the vagina, and on which vaginal moisture has been deposited.

Another example of such contacting is spraying of the reactant in sprayable form onto the element 30. A further example of such contacting is flowing of the reactant, in fluid form onto the element 30 to contact vaginal moisture. The fluid reactant or reactants discharge from a fluid container or containers.

FIG. 9 also: represents an optional confirmation step of obtaining a visual comparison of the color changed zone on the receiver 30 with a color, or different colors, or band color shades, where one color band may indicate presence of putrecine; another color band may indicate presence of cadaverine; and a third band may have another color or color shade close to but different from the first two, and so indicating absence of putrecine or cadaverine, i.e. an amine test when compared side-by-side with the color on the receiver 30. Such amine indicates presence of pathogenic bacteria.

As referred to above test element 30 may alternatively comprise a porous body to receive vaginal moisture for use in a subsequent color test, outside the body. Two or more test elements, as described, may be incorporated on the probe. A second such element appear at 130, in FIG. 7.

Referring again to FIG. 1, it shows provision of a notch or notches 44 proximate the root end of the probe, for reception of a latching component 45 on a sleeve that receives the probe. See FIG. 8 showing such a latch 45 received into the notch, to temporarily and protectively retain the probe in sleeve 42. The interlock allows forcible endwise removal of the probe from the sleeve, at the time of use, the sleeve body deflecting to enable later release. Two such notches 44 are provided, at opposite sides of the probe in FIG. 1, so that if the probe is inserted laterally upside down, the latch 45 will enter the other notch.

I claim:

1. Vaginal probe apparatus comprising, in combination
   a) a longitudinally elongated probe insertible into the vagina, for a test purpose,
   b) a support operatively connected with the probe projecting away from the support,
   c) the support including:
      v) a manually manipulable handle having a generally flat side with lateral width,
      vi) an edge presented generally longitudinally for limiting probe insertion into the vagina,
   d) and at least one vaginal moisture wettable test element on at least one outer side of the probe, to extend generally parallel to said handle flat side, and with substantially reduced lateral width relative to said handle flat side lateral width,
   e) said side of the probe having lateral width less than about one-half the lateral width of the handle, and the handle and probe having key-like configuration.

2. The combination of claim 1 including surface irregularities on the support for engagement by the thumb or finger of a user.

3. The combination of claim 2 wherein said support has a laterally facing side at which said irregularities are located.

4. The combination of claim 3 wherein said irregularities extend generally longitudinally.

5. The combination of claim 3 wherein said irregularities define protuberances at said support side.

6. The combination of claim 1 wherein said probe has a length "l" between 1½ and 2½ inches.

7. The combination of claim 1 wherein l≅2 inches.

8. The combination of claim 1 wherein said probe has a width "$w_1$" between ¼ and ½ inch and said support has a width "$w_2$"=¾ to 1½ inch.

9. The combination of claim 8 wherein $w_1 \cong$ ⅜ inch.

10. The combination of claim 1 wherein said probe has an approximately flat oval cross section.

11. The combination of claim 10 wherein said probe has a length "l" between 1½ and 2½ inches.

12. The combination of claim 1 including at least one vaginal moisture wettable test element on the probe.

13. The combination of claim 12 wherein said element comprises an indicator element.

14. The combination of claim 13 wherein said indicator element is one of the following:
   i) a pH indicator
   ii) an amine indicator
   iii) a bacteria indicator.

15. The combination of claim 1 wherein the probe has an oval cross section.

16. The combination of claim 1 including at least one locking projection on the probe, and between the handle and probe to interlock with a storage sheath into which the probe is receivable.

17. The combination of claim 16 including said sheath receiving said probe.

18. The combination of claim 1 wherein the probe and support define a single body.

19. The combination of claim 18 wherein said body consists essentially of molded plastic material.

20. The combination of claim 12 wherein there are at least two of said test elements on the probe.

21. The combination of claim 20 wherein one of said elements is a color change indicator and the other element is moisture absorbent, for use in testing externally of the vagina.

22. The combination of claim 1 wherein said probe defines a longitudinally extending axis which substantially bisects said support.

23. The combination of claim 6 wherein said probe defines a longitudinally extending axis, and said support extends eccentrically, relative to said axis.

24. The combination of claim 1 wherein at least one notch is provided in the probe, at or proximate the root end,of the probe, for reception of a latching component on a sleeve, receiving the probe.

25. The combination of claim 24 wherein two such notches are provided, at opposite sides of the probe.

26. Vaginal probe apparatus comprising, in combination
   a) a longitudinally elongated probe insertible into the vagina, for a test purpose,
   b) a support operatively connected with the probe projecting away from the support,
   c) the support including:
      v) a manually manipulable handle having a generally flat side with lateral width,
      vi) an edge presented generally longitudinally for limiting probe insertion into the vagina,
   d) and at least one vaginal moisture wettable test element on at least one outer side of the probe, to extend generally parallel to said handle flat side, and with substantially reduced lateral width relative to said handle flat side lateral width,
   e) the handle and probe having generally key-like configuration.

* * * * *